(12) United States Patent
Hodos

(10) Patent No.: US 6,623,243 B1
(45) Date of Patent: Sep. 23, 2003

(54) MINIMIZATION OF MOTION SMEAR: AN APPROACH TO REDUCING AVIAN COLLISIONS WITH WIND TURBINES

(75) Inventor: William Hodos, Chevy Chase, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/959,566

(22) PCT Filed: Apr. 28, 2000

(86) PCT No.: PCT/US00/11682
§ 371 (c)(1),
(2), (4) Date: Oct. 30, 2001

(87) PCT Pub. No.: WO00/66889
PCT Pub. Date: Nov. 9, 2000

Related U.S. Application Data
(60) Provisional application No. 60/131,800, filed on Apr. 30, 1999.

(51) Int. Cl.[7] ............................. F03D 1/06; F03D 11/00
(52) U.S. Cl. ...................... 416/61; 416/146 R; 351/237
(58) Field of Search ................. 416/5, 61, 62, 416/146 R; 351/205, 206, 211, 214, 223, 237; 359/522

(56) References Cited

U.S. PATENT DOCUMENTS

| | | | | | |
|---|---|---|---|---|---|
| 1,035,431 A | * | 8/1912 | Ericson | .......................... | 416/9 |
| 1,747,433 A | * | 2/1930 | Genest | .......................... | 416/5 |
| 1,882,163 A | * | 10/1932 | Ross | .......................... | 416/223 R |
| 2,466,787 A | * | 4/1949 | Whisler et al. | ................ | 416/99 |
| 2,701,540 A | * | 2/1955 | Hamilton | ........................ | 416/5 |
| 2,918,671 A | * | 12/1959 | Halpern | .......................... | 416/5 |
| 6,082,868 A | * | 7/2000 | Carpenter | ..................... | 416/5 |

FOREIGN PATENT DOCUMENTS

| | | | | | |
|---|---|---|---|---|---|
| JP | 56-113096 A | * | 9/1981 | ..................... | 416/5 |
| JP | 5-202890 A | * | 8/1993 | ..................... | 416/5 |

* cited by examiner

Primary Examiner—Christopher Verdier
(74) Attorney, Agent, or Firm—Dykema Gossett, PLLC (57) ABSTRACT

A method and apparatus for reducing avian collisions with wind turbines 70, wherein a design or pattern 90 is placed on the rotor blades 60 of a wind turbine 70 for reducing the motion smear of the image of the rotor blades 60 on the bird's retina 30. When the motion smear on the bird's retina 30 is reduced, the bird 10 is capable of detecting the presence of the rotor blades 60 more easily, thus allowing the bird 10 to re-direct its flight path and avoid colliding with the wind turbine 70. The design principle is that a pattern placed in a given location on one rotor blade 60 is not repeated in the same location on any other rotor blades 60 on the wind turbine 70.

21 Claims, 7 Drawing Sheets

| A. BLADE VELOCITY (RPM) | B. BLADE-TIP VELOCITY (M/SEC) | C. BLADE-TIP VELOCITY (DEG/SEC) | D. BLADE-TIP RETINAL-IMAGE VELOCITY (DVA/SEC) |
|---|---|---|---|
| 36 | 1.2 | 216 | 115 |
| 48 | 1.6 | 288 | 153 |
| 56 | 1.9 | 336 | 179 |
| 66 | 2.2 | 396 | 211 |
| 80 | 2.7 | 480 | 256 |
| 96 | 3.2 | 576 | 307 |
| 105 | 3.5 | 630 | 336 |
| 144 | 4.8 | 864 | 460 |
| 156 | 5.2 | 936 | 499 |

FIG. 9

| # | PATTERN TYPE | DESCRIPTION |
|---|---|---|
| 1 | NOISE | BOTH EYES COVERED; NO VISUAL STIMULATION |
| 2 | BLANK | WHITE BLADES WITHOUT STRIPES |
| 3 | NON-STAGGERED (THIN) | THE SAME THIN-STRIPE PATTERN ON EACH BLADE |
| 4 | STAGGERED THIN | ANTI-MOTION-SMEAR; THIN STRIPES |
| 5 | STAGGERED (THICK AND THIN) | ANTI-MOTION-SMEAR; THICK STRIPES FROM CENTER OF BLADE TO HUB; THIN STRIPES FROM CENTER TO TIP |
| 6 | SINGLE-BLADE (THIN) | ANTI-MOTION-SMEAR; THIN STRIPES ON ONE BLADE; TWO BLADES BLANK |
| 7 | SINGLE-BLADE (THICK AND THIN) | ANTI-MOTION-SMEAR; THICK STRIPES FROM FROM CENTER OF BLADE TO HUB; THIN STRIPES FROM CENTER TO TIP ON ONE BLADE; TWO BLADES BLANK |
| 8 | SINGLE-BLADE (SOLID BLACK) | ANTI-MOTION-SMEAR; ONE BLADE SOLID BLACK; TWO BLADES BLANK. |

MINIMIZATION OF MOTION SMEAR: AN APPROACH TO REDUCING AVIAN COLLISIONS WITH WIND TURBINES

CROSS-REFERENCE TO RELATED APPLICATION

This application is a U.S. national phase of PCT/US00/11682, filed Apr. 28, 2000, which claimed priority of U.S. Provisional Application 60/131,800, filed Apr. 30, 1999.

BACKGROUND OF THE INVENTION

1. Field of the Invention

This invention relates generally to a method for causing behavioral modifications in animals by altering retinal responses, and more particularly to a method for marking wind turbines so as to alter the motion smear blur that moving elements such as wind turbines create in avians and thereby cause the avians to alter their flight paths and avoid collisions with the wind turbines.

2. Description of Related Art

The development of wind power as a source for the generation of electricity has led to the establishment of "wind farms," such as Altamont Pass, Calif. where thousands of wind turbines have been erected. While generally conceded to be environmentally safe, wind turbines have been reported to be hazardous to flying birds. The birds cannot effectively see the wind turbines when they are rotating, and they fly into the moving turbines and are maimed or killed. The present invention provides a principle for designing blade patterns to deter collisions of the birds with the wind turbines.

Motion smear is the degradation of the visibility of rapidly moving objects that results from the inability of the retina of the eye to process the high temporal frequencies of stimulation that result from high velocities of retinal-image motion. In the case of wind turbines, motion smear occurs primarily at the tips of the blades, making them deceptively transparent at high retinal-image velocities. Attempts to minimize motion smear must take into account its causes and attempts to reduce the temporal frequency of stimulation of the retinal. Anti-motion smear patterns are designed to do this by not repeating a pattern in one location on a turbine blade at the same location on any other blade. In a three-blade turbine, the temporal frequency of stimulation is thereby reduced by a factor of three.

To simulate turbines in a laboratory, a variable speed motor is used to spin an array of three blades with a diameter of 64 cm. The blades with anti-motion smear patterns are compared with blades that have no patterns or blades with patterns that are not staggered to reduce the temporal frequency of stimulation. Because this apparatus is relatively close to the subject's eye, it is possible to simulate retinal-image velocities that would occur in a real environment with wind turbines having diameters of 20 m or more. In the method herein described, the subjects used were American kestrels (Falco sparverius). Each kestrel was anesthetized and electrodes were inserted under the eye lids in contact with the cornea to record the pattern electroretinogram (PERG) from the retina. The amplitude of the PERG in microvolts was the measure of pattern visibility.

Data show that anti-motion smear patterns produce a higher PERG amplitude, which translates into a higher pattern visibility at a given distance. For example, at a retinal velocity of 120 deg. of visual angle/sec, the most effective anti-motion smear patterns produce PERG amplitudes that were three times the amplitude of the blades with no patterns. A single, solid black blade, paired with two white blades, is one of the most visible stimulus, because it may stimulate a larger area of the retina than striped blades. Even though the anti-motion smear patterns are more visible at a distance of approximately 25 m than blank blades or blades with unstaggered, repeating patterns, as the bird gets closer to the blades, the retina is unable to process the progressively higher retinal-image velocities and all patterns rapidly lose visibility with decreasing distance.

SUMMARY OF THE INVENTION

It is an object of the present invention to provide a method and apparatus for reducing avian collisions with wind turbines.

Other objects, advantages and novel features of the invention will become more apparent from the following detailed description of the invention when taken in conjunction with the accompanying drawings.

DETAILED DESCRIPTION OF THE INVENTION

Figure 11:
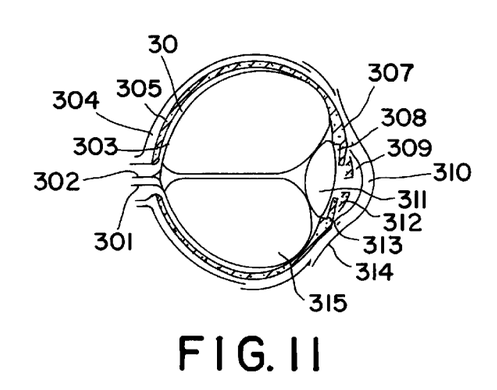
FIG. 11 is a cross-sectional view of an eye.

FIG. 11 depicts a cross section of an eye. It includes an optic nerve 301 with blind spot 302, a fovea 304, a sclera 304, a choroid 305, a retina 30, aciliary body 307, a posterior chamber 308, an anterior chamber 309, a cornea 310, a lens 311, an iris 312, a suspensory ligament 313, a conjunctiva 314, and a vitreous humor 315.

The eyes of birds have universal macularity. This means they have a low ratio of receptors to ganglion cells (4:1–8:1) out to the periphery of the retina 30 of their eye 20. As such, they maintain good acuity even in peripheral vision. In addition, they have specialized receptors in the presence of two foveal regions of the eye 20; one for frontal vision and one for looking at the ground. Moreover, birds 10 have various optical methods for keeping objects at different distances simultaneously in focus on the retina 30.

As an object 130 moves across the retina 30 of the eye 20 with increasing speed, it becomes progressively blurred. This blurring phenomenon is known as "motion smear" or "motion blur" and is well known in human psychophysical research. It results from the fact the human visual system is sluggish in its response to temporal stimulation; i.e., the visual system is sluggish in its response to temporal stimulation; i.e., the visual system summates signals over periods of about 120 msec in daylight. The advantage is that it such a technique enhances visual sensitivity, but at the price of the smearing or blurring of moving targets. In addition, the critical flicker-fusion threshold (the lowest frequency at which a flickering light is perceived as flickering rather than steady) is 2–3 times shorter in birds 10 than in humans. It has been proposed that the human retina has a mechanism for sharpening blurred, moving images. It is possible that birds 10 may have a shorter summation time and this is their mechanism for reducing motion smear.

The phenomenon of motion smear is apparent at the tips 50 of rotor blades 60 on wind turbines 70 turning at the rate of approximately 35 RPM and higher. The more central regions 80 of the rotor blades 60 do not suffer from motion smear. Since both the central regions 80 and the tips 50 are rotating at the same RPM, it seems most likely that the relevant variable is the velocity of the blades 60 at the more peripheral regions 50. The higher velocity of the blade tip 50 has placed it in the temporal-summation zone in which the retina 30 is sluggish in its ability to resolve temporally separated stimuli, whereas the lower velocities of the more central potions 80 are below the transition point and the individual blades 50 can be seen more or less clearly.

A serious problem in attempting to solve the problem of collisions of avains 10 with moving objects is the absence of data on the angle of approach to the blades 60 at the moment of collision. If the birds 10 are struck while approaching the blades 60 from a direction that is parallel to the long axis of the blade 60, then the problem of motion smear is compounded by the very small profile of the blades 60 from that line of sight. A solution to this problem must (1) effectively increase the profile of the blades 60 in this orientation and (2) take into account the causes of motion smear.

A solution to the problem of motion smear is to maximize the time between successive stimulations of the same retinal region. Any type of pattern 90 applied to the blades 60 that does not take this into account will be ineffective. The typical approach is to apply the same pattern 90 to each blade 60, which does nothing to maximize the time between successive stimulations of the same retinal region. The present approach is to use different patterns 90 on each blade 60. The patterns 90 are designed so that a pattern 90 on any given blade region is not repeated on the equivalent region of the other two blades 60. Thus stimulations per second of any given retinal region are reduced by a factor of 3 and the time between stimulations is virtually tripled.

Figure 1:
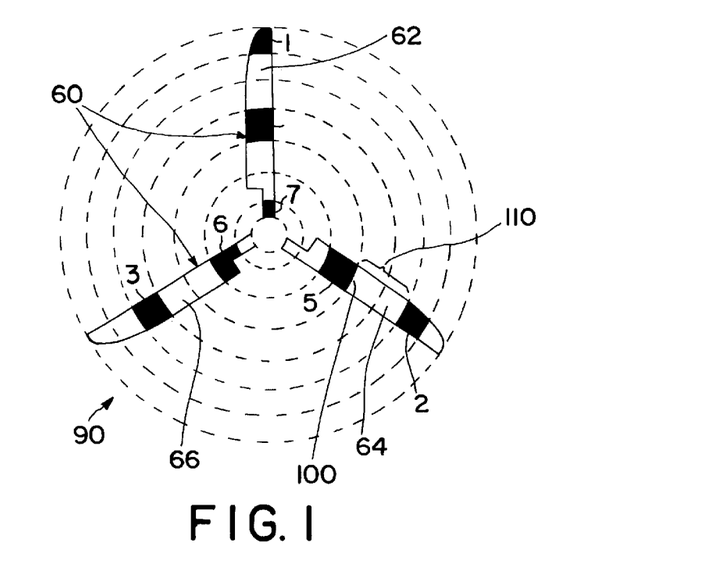
FIG. 1 is a front elevational view of an anti-motion smear pattern of the present invention on a rotor blade, showing thick stripes having different locations on each rotor blade.

FIG. 1 shows an anti-motion smear pattern 90 of black stripes 100 staggered across a blade 60 in such a way that a given stripe 100 appears in only one location on any of the three blades 60. In this example, one blade 62 has stripes 100 in locations 1, 4 and 7. Another blade 64 has stripes in locations 3 and 6, and the third blade 66 has stripes in locations 2 and 5.

Figure 2:
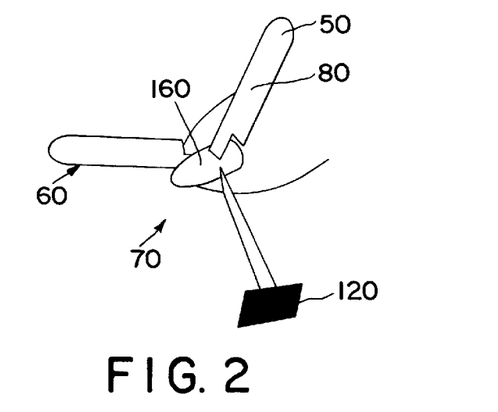
FIG. 2 is a perspective view of a turbine with a design affixed to the tip of a single rotor blade.

The combination of motion smear and a very narrow profile offered by the fast moving tips 50 of rotor blades 60 approached from the side could be quite deadly for a bird 10. A solution to this problem is an attachment 120 connected to the outer tip 50 of the blade 60. This attachment 120, should be painted a solid color such as black and should be fastened so as to be at right angles to the long axis of the blade 60 (FIG. 2). The attachment 120 ideally would be positioned on only one blade 60 to minimize motion smear. Should a single such attachment 120 have sufficient weight to cause an imbalance of the rotor blade assembly, additional attachments could be added to the other two blades 60 for balance. These preferably should be transparent, or at least painted white.

Figure 3:
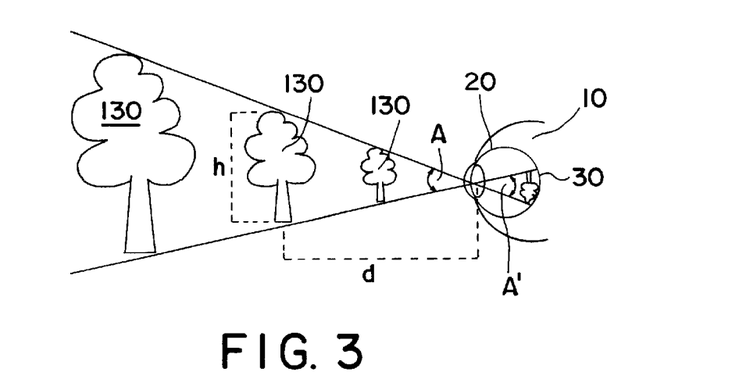
FIG. 3 is an illustration disclosing that objects of different sizes and distances yet have the same angle will cast the same size image on the retina of an eye.

Retinal-image velocity is calculated from the law of the visual angle (visual angle (deg)=57.3×h/d). As may be seen in FIG. 3, all objects 130, at whatever distance, that cast the same size image on the retina 30, subtend the same angle A. The angle A' inside the eye 20 is the same as that from the eye 20 to the object 130. These angles A,A' are called "visual angles" and are the conventional units to describe object size since they are directly related to retinal-image size, which is the only relevant variable for these purposes. In the experiments described below, the tip velocity will be retinal velocity and will be expressed in degrees of visual angle/sec (dva/sec). Degrees of visual angle (dva) are calculated as 57.3×h/d, in which h is the object size (height, width, or area), d is the distance, and 57.3 is the conversion factor from radians to degrees. The advantage of these units is that the tip velocity of a rotor blade 60 many meters in length as seen from a certain distance (i.e. 10–20 m) can be simulated in the laboratory with a much smaller blade 60 located a shorter distance (i.e. 0.5–0.6 m) from the eye 20 and moving at a much higher RPM rate.

In addition to the type, location and configuration of the stimuli, the question of which is the relevant motion variable to consider is important. As discussed above, simple RPM most likely is not a relevant variable because it is the same for both the peripheral 50 and central regions 80 of the blades 60, yet the perceptual effects of the same RPM on each region are very different. This is because the central 80 and peripheral regions 50 of the blades 60 are moving at different velocities.

Figure 4:
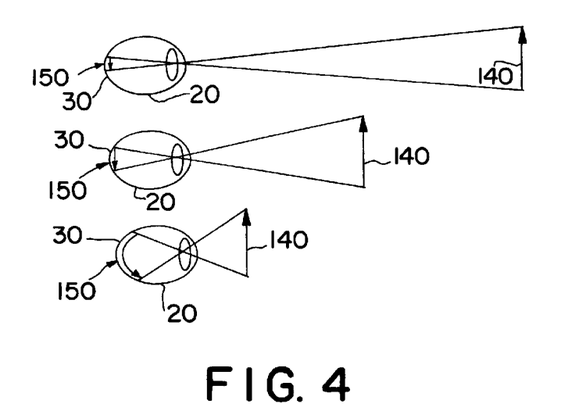
FIG. 4 is a side view showing the relationship of a closer object that is moving perpendicular to the axis of an eye must cover a greater retinal distance in the same period of time than a more distant object.

As is well known in human visual perception, however, the actual velocity of stimulus 130 (the rotor blades 60 in this case) typically is irrelevant; what is crucial is the velocity of the image 150 of the blade 60 as it sweeps across the retina 30 of the eye 20. As the bird 10 approaches the rotor blades 60, the size of their retinal image 150 increases just as a photographic image increases in size as a camera approaches the subject (FIG. 4). This means that as the bird 10 approaches the rotor blades 60, the retinal velocity increases because the tip 50 of the blade 60 must cover a greater distance in the same time. This is related to the phenomenon of "motion parallax", which can be observed by looking out the side window of a rapidly moving train or car; objects close to the window race by with great speed and have considerable motion smear, while distant objects move by at a more leisurely pace and remain sharply in focus. Therefore the proper units in which to express the velocity of the rotor blade tips 50 is in units of retinal-image velocity, which take into account the distance as well as the size.

The foregoing discussion should make several points clear: (1) the RPM of the blades 60 tells nothing about the velocity of the image 150 of those blades 60 as they sweep across the retina 30 of the eye 20, and hence their visibility, unless one takes into account the distance; (2) the visibility of a constant-RPM blade 60 will decrease as the observer approaches the blade 60 due to motion smear; and (3) even though the stimulus display is minuscule in comparison to the actual size of a wind-turbine rotor blade 60, because of the very short viewing distance, the retinal image sizes and retinal velocities are comparable.

Behavioral psychophysical methods to determine the optimal parameters of the patterns 90 to minimize motion smear are extremely slow, time consuming and labor intensive. A more rapid method, that has been used for psychophysical purposes is the pattern electroretinogram or PERG which is generated whenever there is a local contrast change on the retina 30, such as would be produced by a black bar or stripe 100 moving across the retina 30. The PERG would be generated as the retinal area went from lighter to darker as the leading edge of the bar or stripe 100 entered it and again as it went from darker to lighter as the trailing edge exited it. Similar effects would be achieved by the image of a rotating blade 60 as it passed a given retinal area. Blank rotor blades 170 should generate a lower PERG amplitude than striped blades 62,64 because they have a lower contrast against the background than do the stripes 100, which have nearly 100% contrast. In this case, contrast is defined as $(L_L-L_D/L_L+L_D) \times 100$, in which $L_L$ is the luminance of the brighter area and $L_D$ is the luminance of the dimmer area. The pattern electroretinogram has been used to measure visual acuity, contrast sensitivity and a variety of other psychophysical indicators.

The PERG was recorded and analyzed by an ENFANT electrophysiology system (Neuroscientific Corp., Farmington, N.Y.). This instrument is capable of presenting a wide range of visual stimuli 130 on a video display monitor and recording, amplifying, displaying, and analyzing electrical potentials such as those generated by the PERG. Among the analytical techniques available on this instrument are signal averaging, curve fitting, variable highpass and low-pass filtering, various regression analysis, Fourier analysis of frequency components, and others.

To produce the simulated blade stimuli, a variable-speed motor was fitted with 32 cm long rotor blades made from 5 mm white foam board. These were displayed against a background of the same material to provide a worst case, minimal contrast situation between blades 60 and the background. Additional sets of blades 60 of the same material also were prepared with black stripes 100 positioned according to variations on the principle displayed in FIG. 1. The diameter of the circle formed by the outer tips 50 of the blades 60 (64 cm), at a viewing distance of 60 cm, formed a retinal image 150 that subtended a visual angle of 61.6°. The birds 10, however, saw only the lower half of this circle, so the angular subtense of the display that they saw was approximately 30.60. This would be the same size retinal image 150 as a 20 m diameter rotor blade would make at a distance of 19 m.

In order to record the PERG, the animal 10 is lightly anesthetized and its head is placed in a rigid metal head holder. All pressure points are treated with local anesthetic. Platinum electrodes (0.5 mm diameter) are inserted in each upper eyelid so that the electrode makes good contact withe the sclera. Care is taken not to obscure the pupil. A third electrode is inserted in the skin of the scalp to serve as a ground. One eye 20 is covered with a black patch and the electrode in this eye 20 serves as the indifferent electrode. This technique is minimally invasive and the anesthesia depth is lighter than that required for major surgery.

Figure 9:
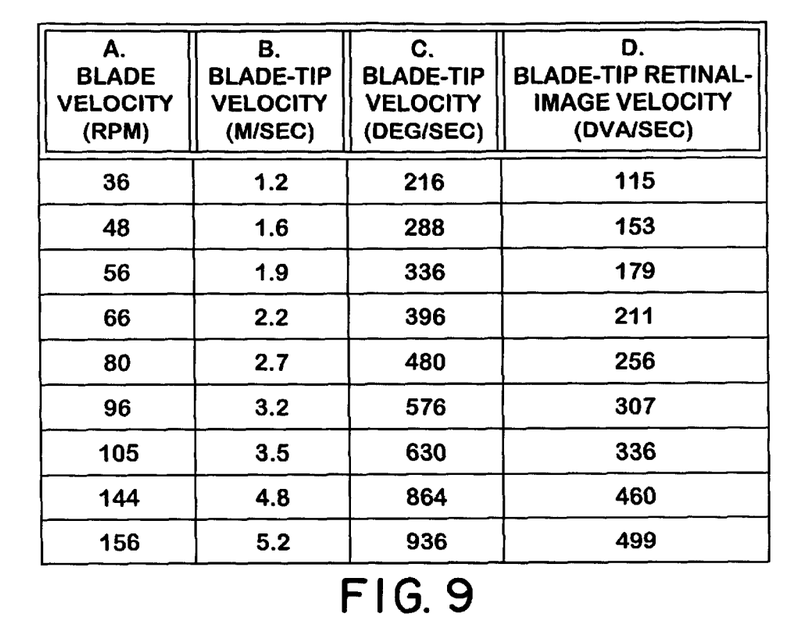
FIG. 9 is a table showing blade velocities and temporal frequencies.

Seven blade velocities ranging from 16–156 RPM were used in the experiment. The table of FIG. 9, shows the blade velocities in RPM, m/sec, and deg/sec, and the velocity of retinal image 150 in degrees of visual angles/sec.

These stimulus parameters model what would occur in the field. For example, a 20 m diameter rotor blade has a circumference of 62.8 m. At 70 RPM, the tip velocity is 4,398 m/min or 263,894 m/hr or 264 km/hr (165 mph) wherein 4,398 m/min equals 73.3 m/sec. The retinal velocity, however, depends on the distance at which the stimulus is viewed. At a distance of 57.3 m, it will have a retinal velocity of 73.3° VA/sec (degrees of visual angle/sec), which is the equivalent of the retinal velocity of a 64 cm diameter stimulus at 45 RPM (Column D in the table of FIG. 9). At a distance of 28 m, however, the 20 m rotor blade will have a retinal velocity of 150 VA/sec, similar to the 48 RPM stimulus, and at 9.1 m, it would have a retinal velocity of 465 VA/sec, similar to the 144 RPM stimulus.

Figure 10:
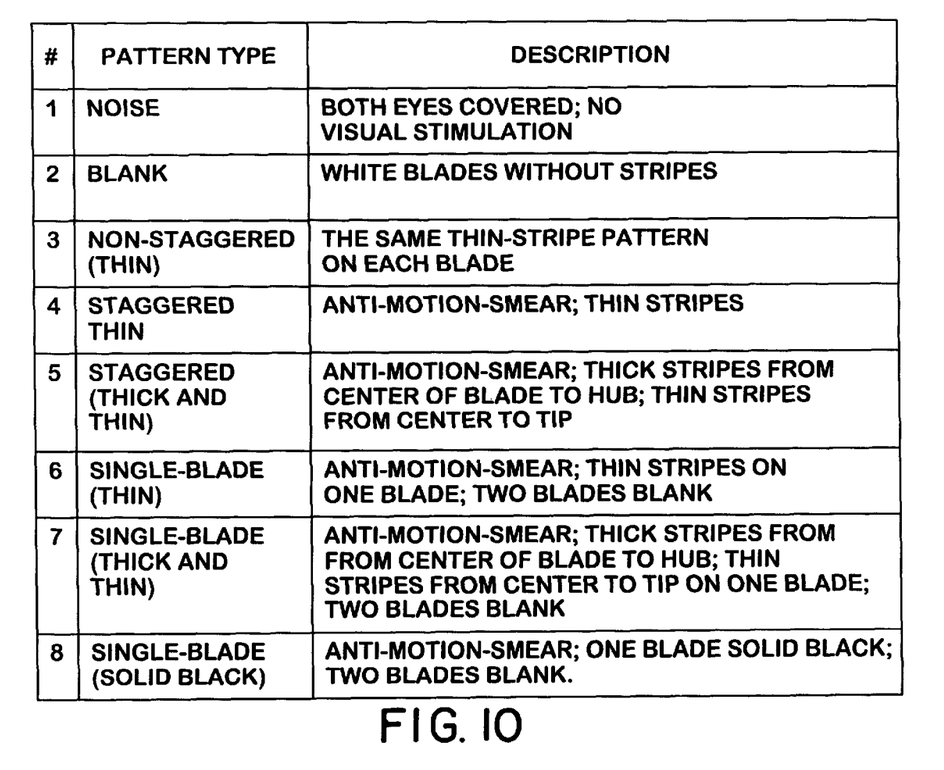
FIG. 10 is a table showing blade designs and their associated descriptions.

The table of FIG. 10 describes the series of patterns 90 that was used in the studies reported here. The baseline against which all blade patterns 90 is compared with is the noise condition, which is the measure of biological noise and ambient electrical noise. The amplitude of the PERG is judged not only in terms of its absolute amplitude in $\mu V$, but also in its relationship to the noise level. The higher the signal-to-noise ratio, the more visible the moving images on the retina 30 are. The standard comparison for the relative visibility of any striped pattern 90 is the PERG amplitude of the blank blades 170, which are intended to simulate the typical, unpatterned, wind-turbine blade array.

Figure 5:
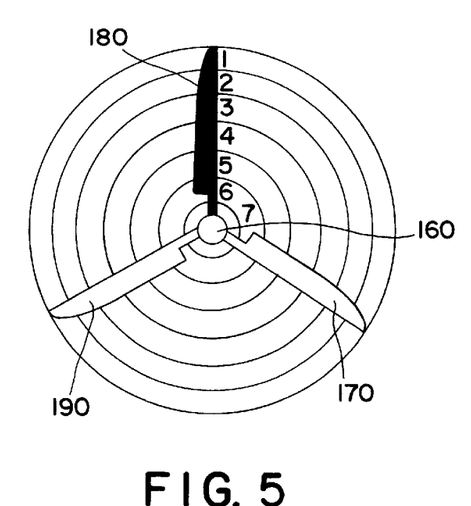
FIG. 5 is a front elevational view of an anti-motion smear pattern of the present invention on a rotor blade, showing one rotor blade solid black and the remaining rotor blades blank.

A way to deal with the different velocities of the central 80 and peripheral regions 50 of the blade 60 would be to have thick stripes 200 between the center 80 of the blade 60 and the hub 160, and thin stripes 190 between the center 80 of the blade 60 and the tip 50. It is also possible to have anti-motion-smear patterns 90 made up only of thin stripes 190 and only of thick stripes 200 or a single black blade 180, paired with two blank blades 170, as illustrated in FIG. 5.

Before conducting any visual experiments, it is vital that a preliminary study of the refractive state of the eye 20 be performed. By determining which corrective lens gives the highest visual acuity (the precise equivalent of an optometric examination), it assures that the image of the stimulus display is in focus on the retina 30. The PERG was used for this procedure as well and the kestrels used in this study were found to be free of refractive errors.

Figure 6:
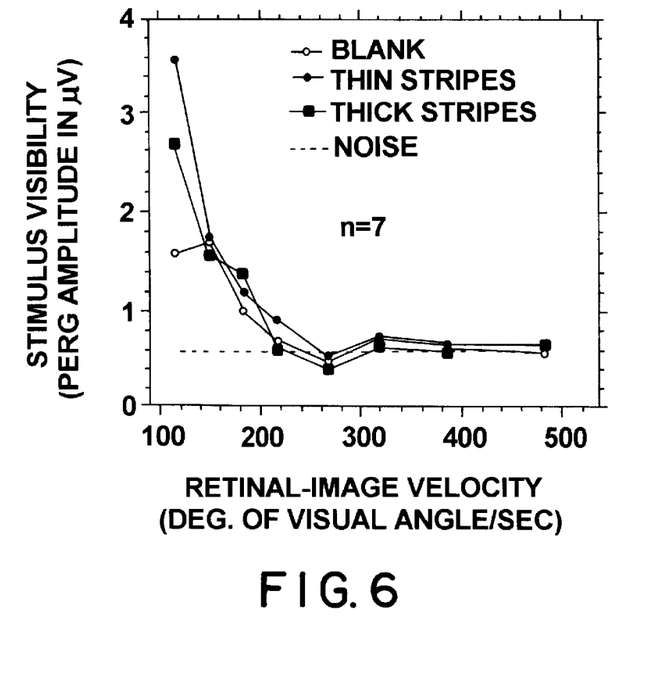
FIG. 6 is a chart showing PERG amplitudes (pattern visibility) as a function of retinal-image velocity for four stimulus types.

Data was collected from four kestrels using the following stimuli: (1) blank blades 170; (2) blades with thin stripes 190 in a staggered pattern; (3) blades with thick stripes 200 in a staggered pattern; and (4) no stimulus; i.e., the eyes 20 are covered so that they could not see the blades 60 or anything else. FIG. 6 shows the mean results of seven recording sessions with each of the four types of stimulus configuration. The figure plots the mean amplitude (n=7) of the pattern electroretinogram (PERG) in $\mu V$ as a function of the velocity of the retinal image 150 of the blade 60 as it sweeps across the retina 30. Retinal velocity is in degrees of visual angle per second (dva/sec). Later in this discussion, the retinal velocity will be translated into practical terms that are of relevance to a bird 10 approaching a moving wind turbine 70.

In FIG. 6, the dotted line indicates the average PERG amplitude when the eyes 20 are closed, which represents the level of biological noise and hence no visibility. It is assumed that the visibility varies linearly with the PERG amplitude that is above the noise level. Thus, doubling the amplitude above the noise level represents a doubling of visibility. The noise level is approximately 0.6 $\mu V$. If PERG amplitude above noise varies linearly with visibility, then for blank blades 170, the visibility at 118 dva/sec is about 1.0 (1.6 $\mu V$ minus 0.6 $\mu V$). By about 185 dva/sec the visibility has dropped in half, and by about 220 dva/sec it has dropped to zero (i.e., to the noise level). In contrast, the thick stripes 200 have a visibility of 2.05 (2.6 $\mu V$ minus 0.6 $\mu V$) at 118 dva/sec, whereas the thin stripes 190 have a visibility of 3.0 (3.6 $\mu V$ minus 0.6 $\mu V$) at the same retinal image velocity. Thus the blades 60 that are patterned with thin, staggered stripes 170 have a visibility that is approximately three times greater than the blank blades 170 at 118 dva/sec.

The experiment was also performed at a higher speed of 150 dva/sec. At this retinal velocity, all patterns 90 performed equally poorly. At 220 dva/sec, thick stripes 200 and the blank blades 170 had achieved zero visibility, and the thin stripes 190 had a slight (but probably meaningless) visibility advantage of 0.4. Thereafter, all the stimuli 130 essentially had no visibility as individual blades, but rather appeared as a blur or smear.

Figure 7:
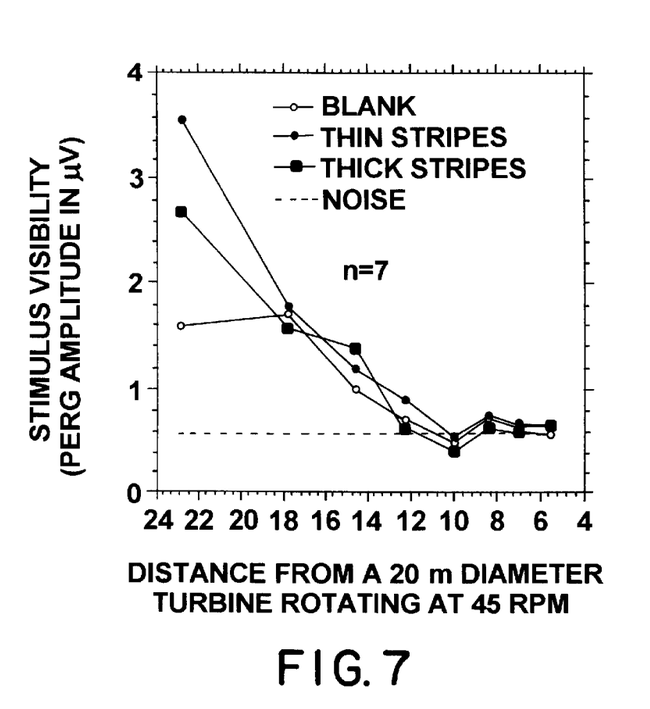
FIG. 7 is a chart showing PERG amplitudes (pattern visibility) as a function of distance for a hypothetical 20 m diameter turbine rotating at 45 RPM.

In FIG. 7, the X-axis has been changed to represent distance d from the eye 20. This conversion is possible because for any moving stimulus 130, the retinal image velocity increases linearly as the distance d to the eye 20 decreases. FIG. 7 shows this conversion for a hypothetical 20 m diameter turbine rotating at 45 RPM. At distances d from the stimulus of 23 m, the three types of stimuli 130 are clearly different, but the difference is gone when the distance shortens to 18 m and closer. By 12 m, the visibility of all the patterns 90 has dropped effectively to zero.

Figure 8:
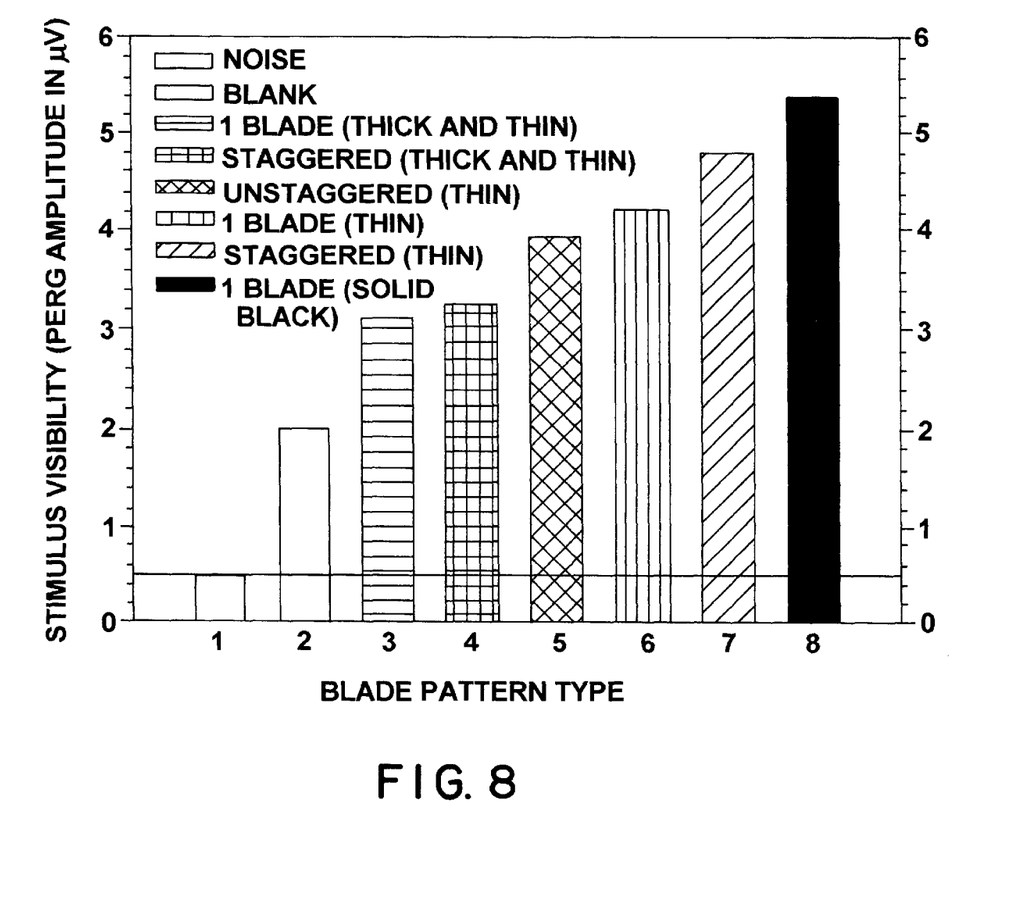
FIG. 8 is a chart showing visibility of blade patterns relative to the noise condition.

FIG. 8 shows the full range of patterns 90 that we have tested thus far. At the present time, these visibility data only have been collected at a retinal-image-velocity of 120 dva/sec and are data from five recording sessions using three kestrels.

Pattern 1 (not shown) represents the noise condition (eyes covered) and, as in FIGS. 1 and 2, constitutes the baseline against which other patterns are compared. In these experiments, the average noise amplitude was 0.42 $\mu V$.

Figure 12:
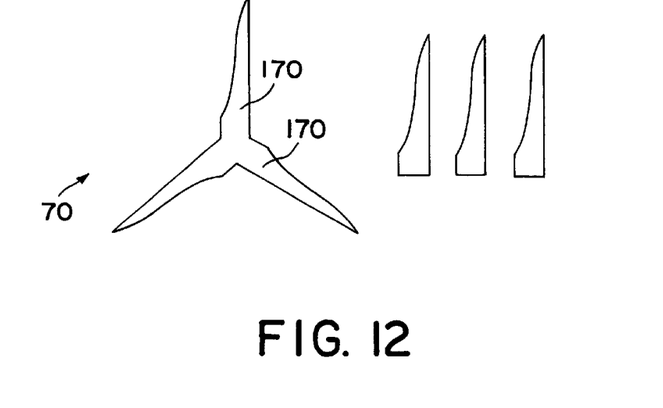
FIG. 12 is a front elevational view of an anti-motion smear pattern of the present invention on a rotor blade, showing all the rotor blades white without stripes.

Pattern 2 (FIG. 12) indicates the PERG amplitude of three blank blades 170, which have a visibility of about 1.6 ($\mu V$ above noise).

Figure 13:
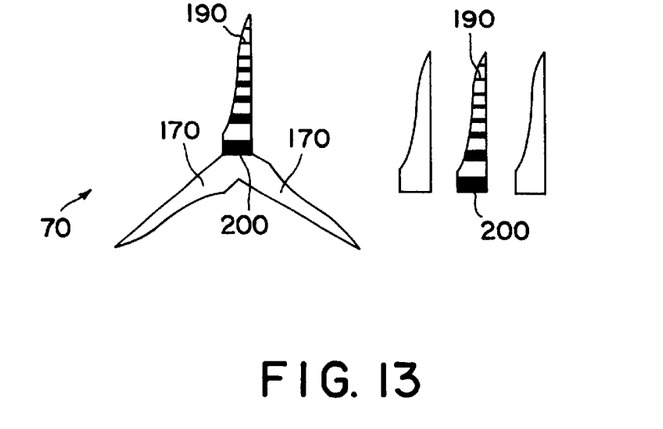
FIG. 13 is a front elevational view of an anti-motion smear pattern of the present invention on a rotor blade, showing the same thin strip pattern on each rotor blade.
Figure 14:
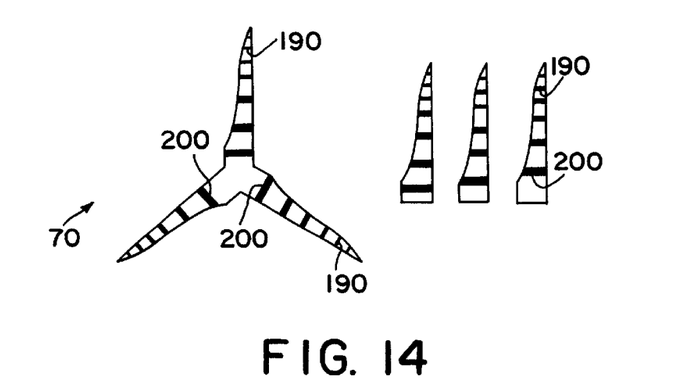
FIG. 14 is a front elevational view of an anti-motion smear pattern of the present invention on a rotor blade, showing thin strips on each rotor blade.

Patterns 3 & 4 (FIGS. 13 and 14 respectively), which had visibilities of about 2.8, were composed of the thick 200 and thin 190, staggered pattern 90. Pattern 3 (FIG. 13) was a single blade pattern 90 and pattern 4 (FIG. 14) was a three-blade pattern 90. The single blade pattern offered no visibility advantage when the stripes 100 were in the thick 200 and thin 190, anti-motion-smear configuration.

Figure 15:
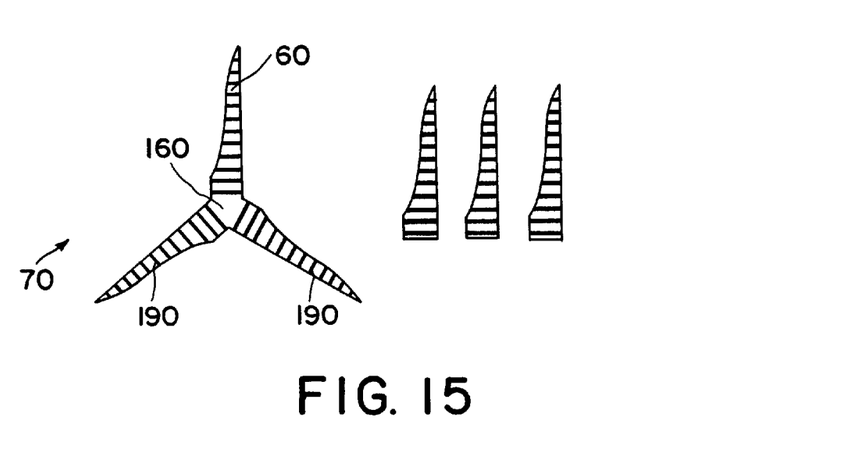
FIG. 15 is a front elevational view of an anti-motion smear pattern of the present invention on a rotor blade, showing thick stripes from the center of the rotor blade to the hub and thin stripes from the center of the rotor blade to the tip.

Pattern 5 (FIG. 15) had thin stripes 100 of uniform thickness on three blades 60. Its visibility was 3.6. This is a blade type that is in experimental use in the Altamont wind area.

Figure 16:
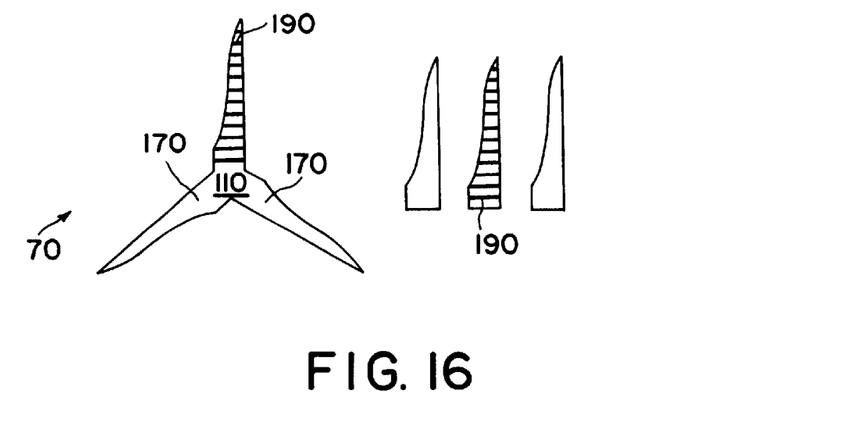
FIG. 16 is a front elevational view of an anti-motion smear pattern of the present invention on a rotor blade, showing thin stripes on one rotor blade and the other two rotor blades blank.

Pattern 6 (FIG. 16), which had the same thin-stripe 190 pattern as pattern 5, except in a single-blade configuration, had a somewhat better visibility of 3.8.

Figure 17:
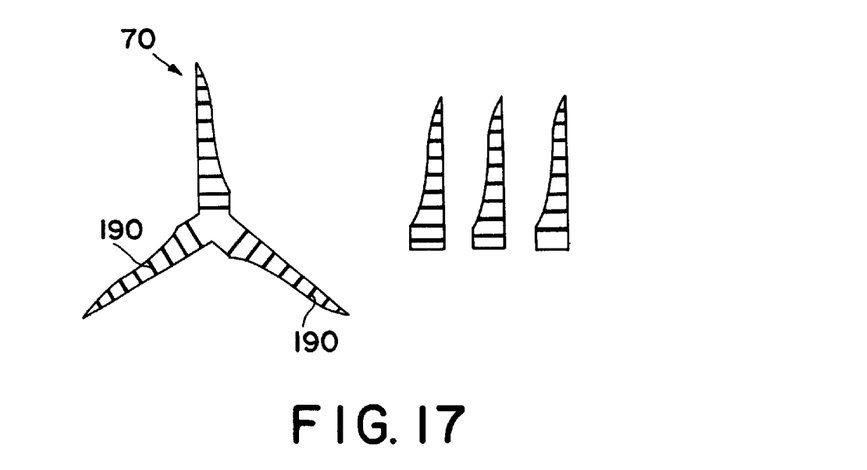
FIG. 17 is a front elevational view of an anti-motion smear pattern of the present invention on a rotor blade, showing thick stripes from the center of the rotor blade to the hub and thin stripes from the center of the rotor blade to the tip with two rotor blades blank.

Pattern 7 (FIG. 17) is the staggered, thin-stripe 190 pattern that was used to collect the data. It has a visibility of 4.4.

Pattern 8 (FIG. 5), which was a single, solid black blade 180, with two blank blades 170 proved to be the most effective stimulus 130. As FIG. 5 shows, this pattern is consistent with the principle of anti-motion-smear patterns 90 in that a given retinal area is stimulated by any particular region on only one of the three blades 60. This pattern had a visibility of 5.0. In physiological terms, it had a signal-to-noise ratio of 12:1, which is the best thus far.

An ideal visual deterrent for avian-turbine collisions is one that continues to provide high visibility as the birds 10 get closer and closer to the whirling blades 60. The analysis of the problem from the velocity detection literature and from the experiments reported here, indicate that the physiology of the retina 30 will not permit such a situation. Beyond a certain point, the velocity of the retinal images 150 of the blades 60 sweeping across the retina 30 will overwhelm the retina's ability to keep up. The initial effect will be a smearing or blurring of the image of the blades 60, and finally their complete transparency, which could appear as an illusory safe place to fly, with deadly consequences for the bird 10. The findings indicate that for a hypothetical turbine with a 20 m diameter blade circumference and rotating at 45 RPM, the anti-motion-smear patterns 90 are quite visible at distances of about 23 m. By 18 m, however, visibility has dropped sharply and no blade pattern, of those tested, has an advantage. By 12 m, visibility has effectively dropped to zero as motion smear and transparency become the dominant visual events.

A kestrel 10 with the wind at its back, could safely maneuver at 25 m. Closer than that, however, would put the bird 10 at risk for not being able to avoid blades 60 should a sudden wind gust push it forward. Moving closer to the blades 60 to about 14.5 m, the blank blades 170 have lost 50% of their visibility at 23 m, and by 10 m, all the blade patterns 90 have become totally blurred.

Good visibility at a distance of approximately 25 m would seem to be a useful deterrent, if low tip visibility is a factor in collisions. On the other hand, since the blade tips 50 at a distance of 10–12 m and closer appear to be transparent blurs, the birds 10 might interpret them as being "safe"; i.e., as the bird 10 gets closer, the threatening looking blades 60 disappear and the bird 10 might feel safe in approaching closer and even trying to fly through the transparent visual smear. In the motion-smear range, an auditory signal might provide some supplementary warning, if it were to be designed with the proper acoustical characteristics that take into account both the hearing capabilities of the various threatened birds and the auditory masking properties of the ambient acoustic environment.

The data on single-blade patterns 90 indicate that a single, solid-black blade 180, paired with two white blades 170 (FIG. 5), is a highly effective, and perhaps the most effective anti-motion-smear stimulus.

The coloring of the blade patterns 90 is a variable that may also aid in preventing bird collisions with wind turbines 70. It has been suggested that if color is important, it probably would only be so at the lower velocities, based on human studies. However, the avian eye, which is much more specialized for color-vision processing than the human eye may have different reactions thereto. Therefore color may offer an advantage over black in increasing visibility at the shorter distances. Also, devices of various size, shape and color may have deterrent effects for lateral approaches to blades 60.

The finding that anti-motion smear patterns increase the visibility of turbine blades 60 at distances at which raptors 10 could safely maneuver away from them should be of interest to various industries that employ structures with moving parts that could pose as hazards to flying birds 10. The data herein described, however, only apply to conditions of bright illumination. It is still unknown to what extent these stimuli retain their improved visibility under sub-optimal viewing conditions, such as mist, rain, etc. Nor will they (or any other visual pattern) retain their visibility once the animal gets close enough for the retinal-image velocity to exceed 200 dva/sec, at which point the bird's retina has passed the limits of its ability to process temporally changing stimuli. Nevertheless, such patterns are worth further investigation to determine whether the visibility advantages they offer will reduce avian mortality.

The finding that a single, solid-black blade 180, paired with two blank blades 170 is the most visible stimulus could have useful economic consequences for wind-power companies that have an interest in testing this type of deterrent. Painting one turbine blade solid black 180 could be much more efficient economically since there would be no requirement for the precision painting of stripes 100 of sizes that would have to vary according to blade diameter and be placed in highly specified positions on each of three blades 60. Instead, the uniform painting of a single blade 60 is all that would be required.

Although particular embodiments of the invention have been described in detail herein with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method of reducing bird collisions with wind turbines having rotor blades, said method comprising the steps of:
   providing a pattern on said wind turbines,
      said pattern being comprised of a plurality of thin and thick stripes,
      said thick stripes being located from a center of each rotor blade to an outer tip of said rotor blade; and
      said thin stripes are located from a center of each rotor blade to an inner hub of said rotor blade; and
      said pattern altering retinal velocity of said wind turbines on said birds;
      said retinal velocity creating motion smear in eyes of said birds; and
   wherein when the motion smear in the eyes of said birds is altered, said birds are capable of detecting the presence of the wind turbines more easily, allowing said birds to re-direct their flight paths and avoid colliding with said wind turbines.

2. An apparatus for altering retinal velocity in animals, comprising:
   a structure having a plurality of moving elements, said moving elements creating a retinal image in eyes of said animals;
   said retinal image having a retinal velocity; and
   a pattern on at least one of said moving elements for altering said retinal velocity in said animals,
      said pattern being comprised of a plurality of thin and thick stripes,
      said thick stripes being located from a center of each moving element to an inner hub of said moving element; and
      said thin stripes are located from a center of each moving element to an inner hub of said moving element; and
   wherein said retinal velocity allows said animals to detect the presence of said structure more easily, which in turn allows said animals to re-direct their paths and avoid colliding with said structure.

3. The apparatus of claim 2, wherein:
   said structures are wind turbines; and
   said moving elements are rotor blades.

4. The apparatus of claim 3, wherein:
   said animals are birds.

5. The apparatus of claim 2, wherein:
   said stripes are staggered on said plurality of moving elements such that each stripe is in a different location than the other stripes on any of said plurality of moving elements.

6. The apparatus of claim 2, wherein:
   said stripes are staggered on said plurality of moving elements such that each stripe is in the same location as the other strip on any of said plurality of moving elements.

7. The apparatus of claim 2, wherein:
   said stripes are located on one moving element only; and
   said other moving elements are blank.

8. An apparatus for altering retinal velocity in animals, comprising:
   a structure having a plurality of moving elements, said moving elements creating a retinal image in eyes of said animals;
   said retinal image having a retinal velocity; and
   a pattern on at least one of said moving elements for altering said retinal velocity in said animals,
      said pattern is comprised of a plurality of thin stripes,
      said thin stripes are located on one moving element only; and
      said other moving elements are blank;
   wherein said retinal velocity allows said animals to detect the presence of said structure more easily, which in turn allows said animals to re-direct their paths and avoid colliding with said structure.

9. A method for causing behavioral modifications in animals by altering retinal responses to stimuli, comprising the steps of:
   providing said animals with eyes capable of having said retinal responses;
   providing said stimuli before said eyes, said stimuli having adjustable parameters and creating said retinal responses in said eyes;
   measuring and evaluating said retinal responses of said eyes;
   adjusting said parameters of said stimuli before said eyes and repeating said step of measuring and evaluating said retinal responses of said eyes;

designating optimal retinal responses from said measured and evaluated retinal responses;

determining parameters of said stimuli for said optimal retinal responses;

duplicating said parameters of said optimal retinal responses on various types of stimuli which said animals will encounter; and wherein said stimuli having said duplicated parameters of said optimal retinal responses allow said animal to more quickly and accurately perceive said stimuli having said duplicated parameters causing said animal to modify its behavior.

10. The method of claim 9, wherein:

said animals are avians;

said stimuli are markings on wind turbines;

wherein said markings having parameters of said optimal responses will cause said avians to alter their behavior in response to seeing said markings on any stimuli.

11. The method of claim 10, wherein:

said parameters are at least one of:
a) size of said stimuli,
b) shape of said stimuli,
c) color of said stimuli,
d) frequency of said stimuli,
e) location of said stimuli,
f) velocity of said stimuli,
g) retinal velocity of said stimuli,
h) distance from a center of said stimuli to its perimeter,
i) number or amount of said stimuli, and
j) distance of said stimuli from said eyes;

wherein said markings causing optimal retinal response will allow said avians to acknowledge said wind turbines quicker than they would without said markings and modify their behavior.

12. A method for detecting and altering motion smears in animals, comprising the steps of:

providing said animals with eyes capable of having said motion smears;

providing a stimuli before said eyes, said stimuli having adjustable parameters and creating said motion smears in said eyes;

measuring and evaluating said motion smears;

adjusting said parameters of said stimuli before said eyes and repeating said step of measuring and evaluating said motion smears;

designating optimal responses from said measured and evaluated motion smears;

determining parameters of said stimuli for said optimal responses; and wherein said parameters of said optimal response can be duplicated on various types of stimuli allowing said animals to more quickly and accurately perceive the stimuli with the duplicated parameters as they encounter it in their natural environment and the animals can then modify their behavior accordingly.

13. The method of claim 12, wherein:

said adjustable parameters are at least one of:
a) size of said stimuli,
b) shape of said stimuli,
c) color and shade of said stimuli,
d) frequency of said stimuli,
e) location of said stimuli,
f) velocity of said stimuli,
g) retinal velocity of said stimuli,
h) distance from a center of said stimuli to a perimeter of said stimuli,
i) number or amount of said stimuli, and
j) distance of said stimuli from said eyes; and wherein changing one or more of said parameters changes said motion smear on said eyes of said animals.

14. The method of claim 13, wherein:

said animals are avians; and said stimuli are markings on wind turbines;

wherein said markings having the same parameters as those of the optimal responses will allow the avians to see said wind turbines earlier than they would without said markings and change their flight path in response to perceiving said markings so as to avoid flying into said wind turbines.

15. A method of reducing bird collisions with a rotating wind turbine having a plurality of blades, comprising the step of coating only one of said plurality of blades with a solid color.

16. A method according to claim 15, wherein said solid color is black.

17. A method according to claim 16, wherein a remainder of said blades are white.

18. An apparatus for altering retinal velocity in an avian animal comprising:

a rotating element having a plurality of blades, said blades vreating a retinal image having a retinal velocity in eyes of said avian animal, only one of said blades being black and a remainder being blank so that, when rotating, the retinal velocity in a flying avian animal is altered, enabling redirection of flight paths and avoidance of collision.

19. The apparatus of claim 18, wherein said remainder blades are white.

20. A method according to claim 16, wherein said rotating wind turbine comprises three blades.

21. An apparatus according to claim 18, wherein said rotating element comprises three blades.

* * * * *